US006951932B2

(12) United States Patent
Moorman

(10) Patent No.: US 6,951,932 B2
(45) Date of Patent: Oct. 4, 2005

(54) SYNTHESIS OF 2-ARALKOXYADENOSINES AND 2-ALKOXYADENOSINES

(75) Inventor: Allan R. Moorman, Durham, NC (US)

(73) Assignee: King Pharmaceuticals Research & Development, Inc., Cary, NC (US)

( * ) Notice: Subject to any disclaimer, the term of this patent is extended or adjusted under 35 U.S.C. 154(b) by 175 days.

(21) Appl. No.: 10/281,291

(22) Filed: Oct. 24, 2002

(65) Prior Publication Data

US 2003/0199686 A1 Oct. 23, 2003

Related U.S. Application Data

(60) Provisional application No. 60/335,169, filed on Oct. 25, 2001, and provisional application No. 60/375,723, filed on Apr. 26, 2002.

(51) Int. Cl.[7] ....................... C07H 19/167; C07H 19/16
(52) U.S. Cl. .................. 536/27.6; 536/26.13; 536/27.1; 536/55.3
(58) Field of Search ............................ 536/27.6, 26.13, 536/27.1, 55.3

(56) References Cited

U.S. PATENT DOCUMENTS 5,140,015 A 8/1992 Olsson et al. .................. 514/46

FOREIGN PATENT DOCUMENTS

| DE | 2258378 | 6/1973 |
| DE | 2324130 | 11/1973 |
| JP | 49-20198 | 2/1974 |
| JP | 49-124096 | 11/1974 |
| JP | 50-53393 | 5/1975 |

OTHER PUBLICATIONS

Marumoto et al., Chem. Pharm. Bull. vol. 23, No. 4, 1975, pp. 759–774.*
R. Marumoto, et al., "Synthesis and Coronary Vasodilating Activity of 2–Substituted Adenosines," Chem. Pharm. Bull., vol.23, No. 4, 1975, pp. 759–774.

R. Olsson, et al., "Synthesis and Cardiac Pharmacology of 2–(AR)Alkoxyadenosines," Nucleosides & Nucleotides, vol. 10, No. 5, 1991, pp. 1049–1055.

H. Schaeffer, et al., "Synthesis of Potential Anticancer Agents. XIV. Ribosides of 2,6–Disubstituted Purines," vol. 80, Jul. 20, 1958, pp. 3738–3742.

M. Ueeda, et al., "Alkoxyadenosines: Potent and Selective Agonists at the Coronary Artery $A_2$ Adenosine Receptor," J. Med. Chem., 1991, vol. 34, No. 4, pp. 1334–1339.

M. Ueeda, et al., "2–Aralkoxyadenosines: Potent and Selective Agonists at the Coronary Artery $A_2$ Adenosine Receptor," J. Med. Chem., 1991, vol. 34, No. 4, pp. 1340–1344.

R. Bartlett, et al., "Synthesis and Pharmacological Evaluation of a Series of Analogues of 1–Methylisoguanosine," J. Med. Chem., 1981, vol. 24, No. 8, pp. 947–954.

K. Miyai, et al., "Synthesis and Anti–Deoxyribonucleic Acid Virus Activity of Certain 9–β–D–Arabinofuranosyl–2–substituted Adenosine Derivatives," J. Med. Chem., 1974, vol. 17, No. 2. pp. 242–244.

* cited by examiner

Primary Examiner—Elvis O. Price
Assistant Examiner—Michael C. Henry
(74) Attorney, Agent, or Firm—Jones Day

(57) ABSTRACT

The invention provides new methods for synthesis of 2-aralkyloxyadenosines and 2-alkoxyadenosines. The invention is particularly useful for synthesis of 2-[2-(4-chlorophenyl)ethoxy]adenosine. Preferred methods of the invention include activating a guanosine compound followed by hydrolysis; alkylating the hydrolyzed compound with subsequent animation to provide a 2-aralkyloxyadenosine or a 2-alkoxyadenosine compound.

80 Claims, No Drawings

SYNTHESIS OF 2-ARALKOXYADENOSINES AND 2-ALKOXYADENOSINES

This application claims the benefit of U.S. provisional patent application No. 60/335,169, filed Oct. 25, 2001 and U.S. provisional patent application No. 60/375,723, filed Apr. 26, 2002, which applications are both incorporated by reference herein in their entirety.

BACKGROUND

1. Field of the Invention

The invention provides new methods for synthesis of 2-aralkyloxyadenosines and 2-alkoxyadenosines. The invention is particularly useful for the synthesis of 2-[2-(4-chlorophenyl)ethoxy]adenosine.

2. Background

Adenosine is an endogenous substance with many biological functions. Many of these biological functions are a result of its role as the natural ligand for the $P_1$ purinergic receptors, also known as adenosine receptors. There are four known subtypes of the adenosine receptor that have been identified and cloned from several mammalian species: $A_1$, $A_{2A}$, $A_{2B}$, and $A_3$. These receptors are prototypical G-protein coupled receptors and elicit their biological activities through typical signal transduction pathways.

Chemical modifications of adenosine have provided molecules which function as either agonists or antagonists and which bind selectively to the individual subclasses of adenosine receptors. The availability of such selective ligands has allowed the many biological functions of adenosine to be attributed to the individual receptor subclasses. In particular, it has been demonstrated that selective adenosine $A_{2A}$ receptor agonists, when applied topically, can significantly accelerate wound healing in animals with both normal and impaired healing capacity. For instance, CGS-21680, a 2-(aralkylamino)adenosine-5'-uronamide, significantly accelerated wound closure in healthy, normal mice (See Montesinos et. al. *J. Exp. Med.*, 1997, 186: 1615–1620). Further, this same compound enhanced healing of excisional wounds in both normal and diabetic rats, compared to untreated rats, an effect that was blocked by the co-administration of a selective adenosine $A_{2A}$ receptor antagonist.

Additional adenosine compounds of interest are the selective adenosine $A_{2A}$ agonists known as 2-alkoxy- and 2-aralkoxy-adenosines. In particular, it has recently been shown that 2-[2-(4-chlorophenyl)ethoxy]adenosine promotes more rapid closure of excisional wounds in normal healthy mice than 0.01% becaplermin gel, an agent currently approved for use in the treatment of diabetic foot ulcers.

The preparation of 2-[2-(4-chlorophenyl)ethoxy]-adenosine and other 2-aralkyloxyadenosines and 2-alkoxyadenosines has involved the displacement of the chloro group of 2',3'-O-(ethoxymethylidene)-2-chloroadenosine or 2',3'-O-(isopropylidene)-2-chloroadenosine with the appropriate sodium or lithium (ar)alkoxide (See Marumoto et al. (1975), *Chem. Pharm. Bull.* 23: 759–774; Ueeda et al. (1991a), *J. Med. Chem.* 34: 1334–1339; Ueeda et al. (1991b), *J. Med. Chem.* 34: 1340–1344), followed by deprotection and purification of the desired product. Blocking of the 2'- and 3'-hydroxyl groups has been described as essential to prevent the formation of a 2→2' polymeric product (Marumoto et al. (1975), *Chem. Pharm. Bull.* 23: 759–774; Ueeda et al. (1991a), *J. Med. Chem.* 34: 1334–1339). It has also been indicated that the liability of the glycosidic N-9→C-1' bond to the acidic conditions required to remove the 2',3'-blocking group contributes to the low yields observed in the preparation of these selective adenosine $A_{2A}$ agonists (Ueeda et al. (1991a), *J. Med. Chem.* 34: 1334–1339).

These synthetic routes are lengthy and often produce compounds in notably low yields. It thus would be desirable to have new methods to synthesize 2-aralkyloxyadenosines and 2-alkoxyadenosines. It would be particularly desirable to have new methods to synthesize 2-[2-(4-chlorophenyl)ethoxy]adenosine.

SUMMARY OF THE INVENTION

We have now found new methods for the preparation of 2-aralkyloxyadenosines and 2-alkoxyadenosines, including compounds of Formula I as that formula is specified below, and pharmaceutically acceptable salts of such compounds. The invention is particularly useful for the synthesis of 2-[2-(4-chlorophenyl)ethoxy]adenosine and pharmaceutically acceptable salts thereof.

Methods of the invention including (a) activating a guanosine compound such as by halogenation; (b) hydrolysis of the resulting compound; (c) treating the hydrolyzed compound resulting with an alkylating agent; and (d) treating the alkylated compound with an amine to provide a 2-aralkyloxyadenosine or a 2-alkoxyadenosine compound.

In a preferred aspect of the invention, a guanosine compound is treated with an acylating agent; the acylated compound is then preferably activated particularly by treatment with a halide source, such as a chloride source, and that compound undergoes a hydrolysis reaction, preferably after treatment with activated nitrogen compound, particularly a compound containing an oxy-nitrogen moiety especially a nitric oxide (NO, $NO_2$, etc.) functionality as exemplified by a nitrite compound; the resulting compound is then treated with an alkylating agent followed by animation such as by treatment with ammonia or other suitable amine. A particularly preferred synthesis provides 2-[2-(4-chlorophenyl)ethoxy]adenosine.

Particularly preferred syntheses of the invention include preparation of 2-[2-(4-chlorophenyl)ethoxy]adenosine by acylation of guanosine with acetic anhydride in dimethylformamide and pyridine, followed by chlorination with phosphorus oxychloride. The resulting intermediate is suitably hydrolyzed following diazotization with tert-butyl nitrite, then alkylated with 2-(4-chlorophenyl)ethyl bromide in dimethylformamide in the presence of cesium carbonate, followed by displacement of the 6-chloro moiety and concomitant deprotection using ammonia in ethanol. The 2-[2-(4-chlorophenyl)ethoxy]adenosine can be isolated in high yields, e.g. about 40 to 50 mole percent based on the 2-amino-6-chloro-9-(2,3,5-tri-O-acetyl-β-D-ribofuranosyl) purine starting material. Similar yields are obtained with other 2-alkoxyadenosines and 2-aralkyloxyadenosines.

DETAILED DESCRIPTION OF THE INVENTION

As stated above, we have now found new methods for the preparation of 2-aralkyloxyadenosines and 2-alkoxyadenosines, including compounds of the following Formula I which can be useful as a selective ligand for adenosine receptors or as an intermediate in the synthesis of selective ligands for adenosine receptors.

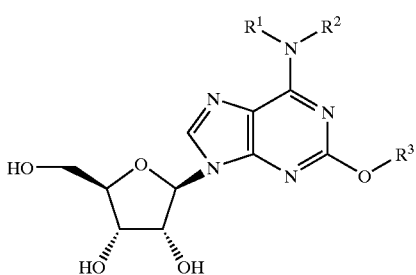

In that above Formula I, $R^1$ and $R^2$ are independently hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aralkyl, substituted aralkyl, aryl, substituted aryl, heteroaryl, heterocyclic, or if taken together with the nitrogen atom, forms an azetidine ring or a 5–6 membered heterocyclic ring containing a total of one to four heteroatoms selected from nitrogen, oxygen, and sulfur;

$R^3$ is alkyl, substituted alkyl, alkenyl, substituted alkenyl, alkynyl, substituted alkynyl, aralkyl, substituted aralkyl, aralkenyl, or substituted aralkenyl.

In one embodiment, a preferred process of the invention comprises treating guanosine with an acylating agent in the presence of a base and a solvent at a suitable reaction temperature of e.g. about 20° C. to about 120° C. for a time sufficient for substantial reaction completion e.g. about 20 minutes to about 30 hours. Suitably, the reaction product is treated in a solvent with a suitable halide source, particularly chloride source, such as phosphorus oxychloride in the presence of a tertiary amine, thionyl chloride/DMF, phosphorus pentachloride, chlorine gas, carbon tetrachloride/triphenylphosphine, dichlorotriphenylphosphorane, or triphenylantimony dichloride at a suitable reaction temperature e.g. reaction temperature of 10° C. to about 120° C. for a time sufficient for substantial reaction completion e.g. for about 5 minutes to about 8 hours.

Conversion of the product from the second step to the corresponding 2-hydroxy-derivative is suitably performed with a nitrite reagent such as an alkyl nitrite or sodium nitrite in the presence of acid e.g. inorganic acid in a suitable solvent such as a mixture of water and a lower alcohol at a suitable temperature to promote reaction e.g. −10° C. to about 60° C. for a period of e.g. about 20 minutes to about 24 hours. The protected 6-chloro-2-hydroxy-9-(β-D-ribofuranosyl)purine in a solvent is added to a suitable alkylating agent, e.g. at a temperature of 0° C. to about 120° C. for a period of about 30 minutes to about 48 hours. The intermediate is dissolved in an alcoholic solvent which is treated with ammonia or a suitable primary or secondary amine at temperatures of −70° C. to about 120° C. for a period of about 20 minutes to about 48 hours and one to fifty atmospheres of pressure. The reaction mixture is evaporated and then the product is purified by recrystallization from a suitable solvent or chromatography or a combination of these two methods.

In accordance with one embodiment, the acylating agent is selected from the group of acetyl chloride, acetic anhydride, propionyl chloride, propionic anhydride, benzoyl chloride, benzoic anhydride, phenylacetyl chloride, and phenoxyacetyl chloride.

The base is selected from the group of pyridine, 4-dimethylaminopyridine, 4-pyrrolidinyl-pyridine, N,N-dimethylaniline, N-ethyl-N-methylaniline, N,N-diethylaniline, trimethylamine, triethylamine, N,N-dimethylethyl amine, N,N-dimethylisopropyl amine, and N,N-diethylmethyl amine.

The solvent is selected from the group of dimethylformamide, dimethylacetamide, pyridine, acetonitrile, tetrahydrofuran, hexamethylphosphoramide, and 1,4-dioxane.

In the second step of the process, the solvent is selected from the group of acetonitrile, dichloromethane, chloroform, carbon tetrachloride, 1,2-dimethoxyethane, tetrahydrofuran, dimethylformamide, hexamethylphosphoramide, 1,4-dioxane, 1,2-dichloroethane, di(ethylene glycol)diethyl ether, and 2-methoxyethyl ether. The tertiary amine is selected from the group of N,N-dimethylaniline, N-ethyl-N-methylaniline, N,N-diethylaniline, trimethylamine, triethylamine, N,N-dimethylethyl amine, N,N-dimethylisopropyl amine, and N,N-diethylmethyl amine.

In the third step, the alkyl nitrite is selected from the group of tert-butyl nitrite, amyl nitrite, iso-amyl nitrite, or n-butyl nitrite. The lower alcohol is selected from the group consisting of methanol, ethanol, 1-propanol, 2-propanol, 1-butanol, 2-butanol, tert-butanol, amyl alcohol, and iso-amyl alcohol. The inorganic acid is selected from the group consisting of hydrochloric acid, hydrobromic acid, nitric acid, and sulfuric acid.

In the fourth step of the process, the solvent is selected from the group of dimethylformamide, dimethylacetamide, dimethylsulfoxide, hexamethylphosphoramide, 1,2-dimethoxyethane, 1,4-dioxane, tetrahydrofuran, and 2-methoxyethyl ether. The base is selected from the group of lithium carbonate, sodium carbonate, potassium carbonate, cesium carbonate, sodium hydroxide, potassium hydroxide, sodium hydride, sodium tert-butoxide, or potassium tert-butoxide.

In the fifth step of one embodiment of the process of the present invention, the alcoholic solvent is selected from the group of methanol, ethanol, 1-propanol, and 2-propanol.

It will be recognized by one skilled in the art that in a process as described above, the selection of a suitable alkylating agent in step (d) will depend upon the 2-alkoxyadenosine or 2-aralkyloxyadenosine to be synthesized and may be selected from the numerous alkyl chlorides, alkyl bromides, alkyl iodides, alkyl methanesulfonates, alkyl trifluoromethane sulfonates, alkyl tosylates, aralkyl chlorides, aralkyl bromides, aralkyl iodides, aralkyl methanesulfonates, aralkyl trifluoromethane sulfonates, and aralkyl tosylates commercially available or synthetically available by methods known in the art. It will also be recognized by one skilled in the art that in a process as described above, the selection of ammonia or a suitable primary or secondary amine in step (e) will equally be guided by the desired 2-alkoxyadenosine or 2-aralkyloxyadenosine to be synthesized and may be ammonia or selected from the numerous primary and secondary amines commercially available or synthetically available by methods known in the art.

As used herein, the term "alkyl" refers to monovalent straight, branched, or cyclic alkyl groups preferably having from 1 to 20 carbon atoms, most preferably 1 to 10 carbon atoms ("lower alkyl"). This term is exemplified by groups such as methyl, ethyl, n-propyl, iso-propyl, n-butyl, iso-butyl, n-hexyl, 2-methylpropyl, 3-methylbutyl, and the like. The terms "alkylene" and "lower alkylene" refer to divalent radicals of the corresponding alkane. Further, as used herein, other moieties having names derived from alkanes, such as alkoxy, alkanoyl, alkenyl, cycloalkenyl, etc., when modified by "lower," have carbon chains of ten or fewer carbon atoms. In those cases where the minimum number of carbons required are greater than one, e.g., alkenyl and alkynyl (minimum of two carbons) and cycloalkyl (minimum of three carbon atoms), it is to be understood that the term "lower" means at least the minimum number of carbon atoms.

As used herein, the term "substituted alkyl" refers to an alkyl group, having from 1 to 5 substituents, and preferably from 1 to 3 substituents, selected from the group consisting of alkoxy, substituted alkoxy, cycloalkoxy, substituted cycloalkoxy, cycloalkyl, substituted cycloalkyl, cycloalkenyl, substituted cycloalkenyl, alkynyl, substituted alkynyl, acyl, amino, aryl, substituted aryl, carboxyl, carboxyalkyl, cyano, fluoro, hydroxyl, halogen, heteroaryl, heterocyclic, nitro, alkylthio, thiol, mono(alkyl)-amino, di(alkyl)amino, mono(substituted alkyl)amino, di(substituted alkyl)amino, unsymmetric disubstituted amines having different substituents selected from alkyl, substituted alkyl, aryl, substituted aryl, aralkyl, and substituted aralkyl, —SO-alkyl, —SO-substituted alkyl, —SO-aryl, —SO-substituted aryl, —SO$_2$-alkyl, —SO$_2$-substituted alkyl, —SO$_2$-aryl, and —SO$_2$-substituted aryl. As used herein, other moieties having the prefix "substituted" are intended to include one or more of the substituents listed above.

As used herein, the term "alkenyl" refers to straight or branched alkenyl groups having from 2 to 20, most preferably from 2 to 10 carbon atoms and having at least 1 and preferably from 1 to 3 sites of alkenyl unsaturation. This term is exemplified by groups such as ethenyl (CH=CH$_2$), 1-propenyl (CH=CH—CH$_3$), 2-propenyl (C(CH$_3$)=CH$_2$), 3-methyl-2-pentenyl (CH$_2$—CH=C(CH$_3$)—CH$_2$CH$_3$), and the like.

As used herein, the term "alkynyl" refers to straight or branched alkynyl groups having from 2 to 20 carbon atoms, most preferably from 2 to 10 carbon atoms and having at least 1 and preferably from 1 to 2 sites of alkynyl unsaturation. This term is exemplified by groups such as ethynyl, 1-propynyl, 2-propynyl, 2-butynyl, 4,4-dimethyl-2-pentynyl, and the like.

As used herein, the term "cycloalkyl" refers to cyclic alkyl groups of from 3 to 20 carbon atoms having a single cyclic ring or multiple rings joined in either a fused or spirocyclic condensation. This term is exemplified by groups such as cyclopropyl, cyclopentyl, cyclohexyl, cyclooctyl, norbornyl, perhydrofluorenyl, adamantyl, and the like.

As used herein, the term "cycloalkenyl" refers to cyclic alkenyl groups of from 5 to 20 carbon atoms having a single cyclic ring or multiple rings joined in either a fused or spirocyclic condensation and having at least 1 and preferably from 1 to 2 sites of alkenyl unsaturation. This term is exemplified by groups such as cyclopentenyl, cycloheptenyl, 1,3-cyclooctadienyl, cycloheptatrienyl, bicyclo[2.2.1]hepta-2,5-dienyl, and the like.

As used herein, the term "aryl" refers to an unsaturated, aromatic, carbocyclic group of from 6 to 20 carbon atoms having a single ring or multiple condensed rings. This term is exemplified by groups such as phenyl, 1-naphthyl, 2-naphthyl, anthracenyl, 1,2-benzanthracenyl, and the like. As used herein, the term "aryl" also refers to those fused-ring hydrocarbons in which the aromatic ring or rings are condensed to additional non-aromatic rings. In this manner, this term is exemplified by groups such as fluorenyl, acenaphthenyl, biphenylenyl, fluoranthenyl, and the like. Unless otherwise constrained by the definition for the aryl substituent, such aryl groups can optionally be substituted with from one to five substituents, preferably one to three substituents, selected from the list given herein.

As used herein, the term "aralkyl" refers to an aryl or substituted aryl group, attached to an alkylene group or substituted alkylene group, where aryl, substituted aryl, alkylene, and substituted alkylene are as defined herein.

As used herein, the term "heterocyclic" refers to a monovalent saturated or unsaturated carbocyclic group having a single ring or multiple condensed rings, from 1 to 15 carbon atoms and from 1 to 5 heteroatoms within the ring or rings, preferably from 1 to 9 carbon atoms and from 1 to 4 heteroatoms within the ring or rings, selected from the group of heteroatoms consisting of nitrogen, sulfur, and oxygen. This term is exemplified by groups such as tetrahydrofuranyl, pyrrolinyl, pyrrolidinyl, oxazolidinyl, thiazolidinyl, imidazolinyl, imidazolidinyl, piperidinyl, piperazinyl, quinuclidinyl, thiomorpholinyl, morpholinyl, dioxolanyl, and the like.

As used herein, the term "heteroaryl" refers to a 5-membered or 6-membered heterocyclic, aromatic group, which can optionally be fused to an aryl or substituted aryl ring, where heterocyclic, aryl, and substituted aryl are as defined herein. This term is exemplified by groups such as pyrrolyl, furanyl, thiophenyl, pyrazolyl, imidazolyl, isoxazolyl, oxazolyl, isothiazolyl, thiazolyl, thiadiazolyl, triazolyl, tetrazolyl, pyridyl, pyridazyl, pyrimidyl, indolyl, benzofuranyl, benzotriazolyl, quinolinyl, isoquinolinyl, and the like. Optionally, the heteroaryl group may be fused to a second or third heteroaryl group. In this context, this term is exemplified by groups such as 1,2,3-triazolo[4,5-b]pyridinyl, s-triazolo[1,5-a]pyrimidinyl, pyrazolo[3,4-d]pyrimidinyl, purinyl, pterinyl, pteridinyl, pyrimido[5,4-d]pyrimidinyl, and the like.

As used herein, the term "acyl" refers to the groups alkyl-C(O)—, substituted alkyl-C(O), cycloalkyl-C(O), substituted cycloalkyl-C(O), aryl-C(O), substituted aryl-C(O), heterocyclic-C(O), and heteroaryl-C(O), where alkyl, substituted alkyl, cycloalkyl, substituted cycloalkyl, aryl, substituted aryl, heterocyclic, and heteroaryl are as defined herein.

As used herein, the term "alkoxy" refers to the group "alkyl-O—", "substituted alkyl-O—", "cycloalkyl-O—", or "substituted cycloalkyl-O—" where alkyl, substituted alkyl, cycloalkyl, and substituted cycloalkyl are as defined herein. This term is exemplified by such groups as methoxy, ethoxy, 1-propoxy, 2-propoxy, 1-butyloxy, tert-butyloxy, cyclopentyloxy, cyclohexylethoxy, and the like.

As used herein, the term "halo" or "halogen" refers to fluoro, chloro, bromo, and iodo.

As to any of the above groups that contain one or more substituents, it is understood by those skilled in the art, that such groups do not contain any substitution or substitution patterns which are sterically unfeasible and or synthetically impracticable.

All documents mentioned herein are incorporated herein by reference. The following non-limiting examples are illustrative of the invention:

EXAMPLE 1

Synthesis of 2-[2-(4-chlorophenyl)ethoxy]adenosine

Step A: Preparation of 2',3',5'-Tri-O-acetylguanosine

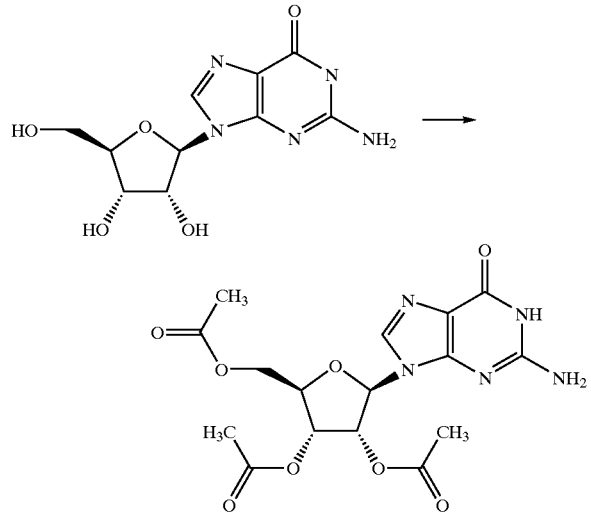

A 12-liter, 3-necked, round bottom flask equipped with a mechanical stirrer, dropping funnel, condenser, and argon inlet is charged with dimethylformamide (9 liters) and guanosine (predried for 20 hours at 80° C. over $P_4O_{10}$, 988 g, 3.50 moles), then heated to 60° C. Pyridine (1.1 liters) followed by acetic anhydride (2.15 liters, 22.8 moles) is added and the mixture heated to 90–100° C. for 4 hours. After cooling to room temperature overnight, the mixture is evaporated to remove approximately 6 liters, then slurried with 10 liters of isopropanol while heating to 70° C. for 1 hour. The mixture is slowly cooled to room temperature, affording the product as a crystalline solid. After collecting by filtration, the solid is washed with isopropanol (2×2 liters), then dried under vacuum at 80° C. for 17 hours to provide the desired intermediate (1,080 g, 75%).

Step B: Preparation of 2-Amino-6-chloro-9-(2,3,5-tri-O-acetyl-β-D-ribofuranosyl)purine

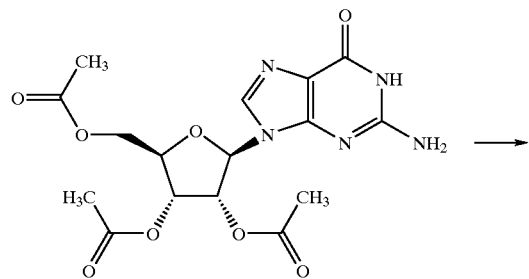

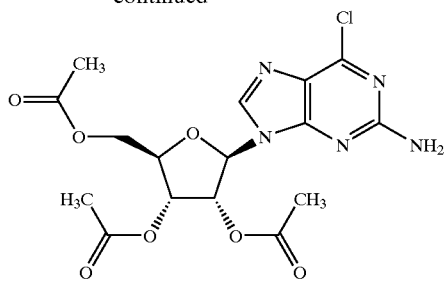

An 8-liter, 3-neck, round bottom flask equipped with a mechanical stirrer, a condenser, a thermometer, and an argon inlet is charged with dry acetonitrile (2.2 liters) and 2',3',5'-tri-O-acetyl-guanosine (550 g, 1.344 moles). Tetraethylammonium chloride (423 g, 2.55 moles), previously dried for 18 hours over $P_2O_5$ at 110° C./high vacuum is added to afford a clear, green solution. After heating to 45–50° C., N,N-dimethylaniline (179 g, 1.48 moles) is added, followed by phosphorus oxychloride (825 g, 5.38 moles) over 15 minutes, during which the temperature rose to 75±3° C. The mixture was kept at 75±3° C. for 15 minutes, flash evaporated ($T_{Bath}<40°$ C.), and the dark red residue taken up in dichloromethane (4 liters). With vigorous stirring, the mixture is washed with ice water (2.5 L), the organic phase is collected, and the aqueous phase extracted with additional dichloromethane (2×1 L). The combined organic phases are washed with cold water (2×2 liters), saturated aqueous $NaHCO_3$ (2×2 L), dried ($Na_2SO_4$), filtered, and concentrated to approximately 1.5 liters. Absolute ethanol (1.5 L) is added and the mixture concentrated to approximately 2 liters. Upon cooling to room temperature, the product crystallizes as a colorless solid (321 g, 56%) after drying in vacuo at 40° C. for 17 hours.

Step C: Preparation of 6-chloro-2-hydroxy-9-(2,3,5-tri-O-acetyl-β-D-ribofuranosyl)purine

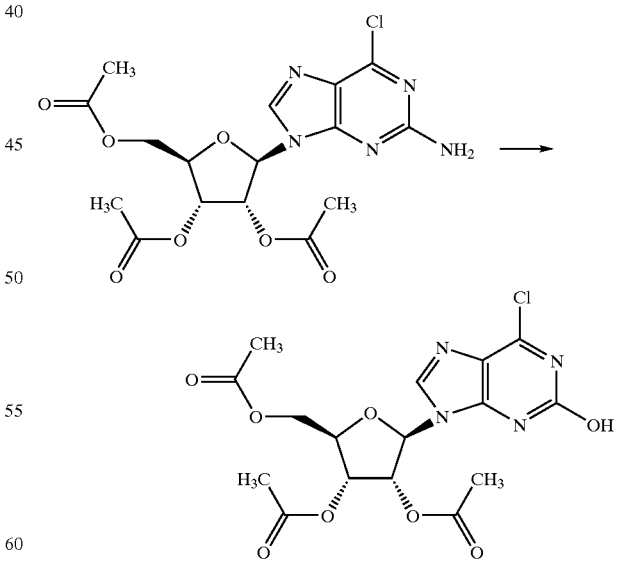

2-Amino-6-chloro-9-(2,3,5-tri-O-acetyl-β-D-ribofuranosyl)purine (42.7 g, 100 mmoles) is dissolved in 2 liters of a tert-butyl alcohol:water mixture (1:1, v/v) with heating. After cooling the solution with an ice bath, tert-butyl nitrite (50 mL, 422 mmoles) is added in one portion.

The ice bath is removed and the mixture is stirred at room temperature until gas evolution ceases (approximately 3 hours). The mixture is then frozen (dry ice/2-propanol) and lyophilized to afford the desired intermediate as a yellow solid that is used immediately or stored frozen at −20° C. without purification.

$^1$H-NMR (DMSO-d$_6$): δ 8.14 (s, 1H, H-8), 6.20 (d, 1H, H-1, J=5.6 Hz), 5.81 (t, 1H, H-2', J=5.5 Hz), 5.57 (dd, 1H, H-3', J=7.5, 4.4 Hz), 4.47–4.42 (m, 3H, H-4', H-5'α, H-5'β), 2.16 (s, 3H, COCH$_3$), 2.15 (s, 3H, COCH$_3$), 2.08 (s, 3H, COCH$_3$).

Step D: Preparation of 6-chloro-2-[2-(4-chlorophenyl)ethoxy]-9-(2,3,5-tri-O-acetyl-β-D-ribofuranosyl)purine

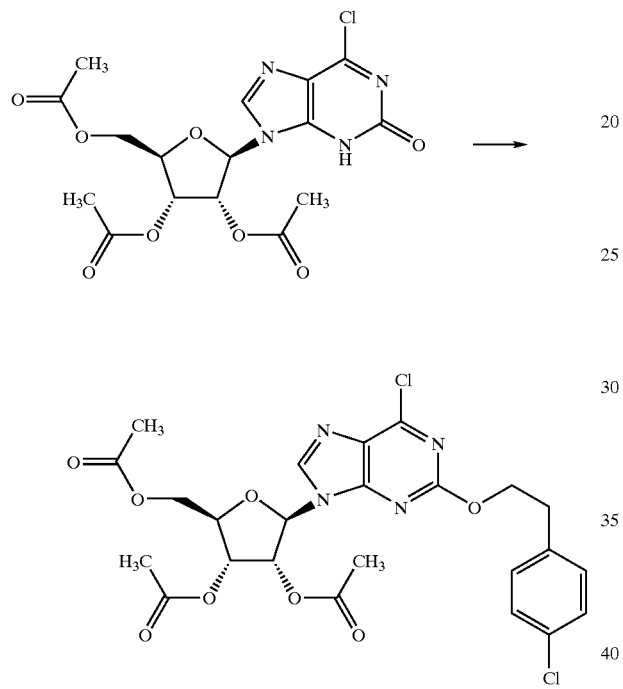

To a solution of crude 6-chloro-2-hydroxy-9-(2,3,5-tri-O-acetyl-β-D-ribofuranosyl)-purine (44.0 g, ca 100 mmoles), dissolved in glass distilled dimethylformamide (2 Liters), is added 2-(4-chlorophenyl)ethyl bromide (43.6 g, 200 mmoles), followed by cesium carbonate (100 g, 307 mmoles). The mixture is stirred at room temperature for 24 hours, evaporated to dryness (T$_{Bath}$<50° C.), and the residue partitioned between dichloromethane (1 liter) and water (1 liter). The organic phase is dried (Na$_2$SO$_4$), filtered, and evaporated. The residue is washed with hexanes (2×500 mL) to remove excess 2-(4-chlorophenyl)ethyl bromide, then dissolved in dichloromethane (250 mL), adsorbed onto silica gel (100 g), and chromatographed over silica gel (1000 g) using a gradient of ethyl acetate (30%→50%) in hexanes. Fractions containing product are collected and evaporated to dryness to afford the desired intermediate as a yellow foam.

Typical yield: 40–70% for Steps C and D combined.

$^1$H-NMR (DMSO-d$_6$): δ 8.06 (s, 1H, H-8), 7.25 (s, 4H, Ar), 6.10 (d, 1H, H-1', J=4.8 Hz), 5.90 (dd, 1H, H-2', J=5.3, 5.0 Hz), 5.62 (dd, 1H, H-3', J=5.3, 5.2 Hz), 4.63–4.56 (m, 2H, OCH$_2$—C), 4.43–4.37 (m, 2H, H-4' & H-5'α), 4.29 (dd, 1H, H-5'β, J=12.0, 4.1 Hz), 3.11 (t, 2H, O—C—CH$_2$—, J=6.9 Hz), 2.10 (s, 3H, COCH$_3$), 2.06 (s, 3H, COCH$_3$), 2.05 (s, 3H, COCH$_3$).

Step E: Preparation of 2-[2-(4-chlorophenyl)ethoxy]adenosine

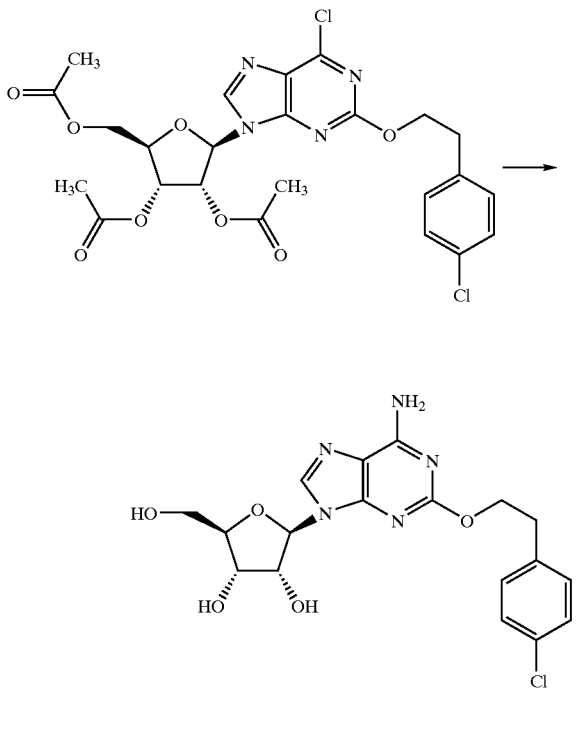

A 2 liter stainless steel autoclave is charged with 6-chloro-2-[2-(4-chlorophenyl)-ethoxy]-9-(2,3,5-tri-O-acetyl-β-D-ribofuranosyl)purine (22.4 g, 39.4 mmoles) and anhydrous ethanol (800 mL) and chilled to −50° C. Liquid ammonia (200 mL) is condensed, added to the autoclave, the autoclave sealed, and the mixture heated to 105±5° C. for 24 hours. The autoclave is then cooled in an ice bath and vented when the pressure drops below 100 psi. After evaporating to approximately 250 mL, activated charcoal (2 g) is added, the mixture heated to reflux for 30 minutes, filtered through Celite®, and evaporated to dryness. The residue is extracted with boiling ethyl acetate (3×250 mL), then partitioned between ethyl acetate (200 mL) and water (250 mL). The final ethyl acetate extraction is washed once with water (100 mL), dried (Na$_2$SO$_4$), filtered, and added to the original ethyl acetate extracts. The combined organic extracts are evaporated to dryness and the solid recrystallized from ethanol (100 mL). The crystalline product is collected by filtration, washed with cold ethanol, and dried at 75° C./2 Torr for 24 hours. A second crop is obtained by concentrating the mother liquor and a third crop may be collected by chromatography of the mother liquor.

Typical yield: 62%

$^1$H-NMR (DMSO-d$_6$): δ 8.14 (s, 1H, H-8), 7.35 (s, 4H, Ar), 7.27 (br. s, 2H, NH$_2$), 5.78 (d, 1H, H-1', J=6.0 Hz), 5.36 (d, 1H, 2'-OH, J=6.2 Hz), 5.12 (d, 1H, 3'-OH, J=4.7 Hz), 5.09 (t, 1H, 5'-OH, J=5.7 Hz), 4.58 (dd, 1H, H-2', J=5.8, 6.3 Hz), 4.40 (t, 2H, OCH$_2$—C, J=6.7 Hz), 4.14 (dd, 1H, H-3', J=4.7, 8.2 Hz), 3.92 (dd, 1H, H-4', J=3.7, 7.3 Hz), 3.65 (m, 1H, H-5'α), 3.54 (m, 1H, H-5'β), 3.00 (t, 2H, O—C—CH$_2$—, J=6.7 Hz).

EXAMPLE 2

Synthesis of 2-[2-(4-chlorophenyl)ethoxy]adenosine

Step C: Preparation of 6-Chloro-2-hydroxy-9-(2,3,5-tri-O-acetyl-β-D-ribofuranosyl)purine

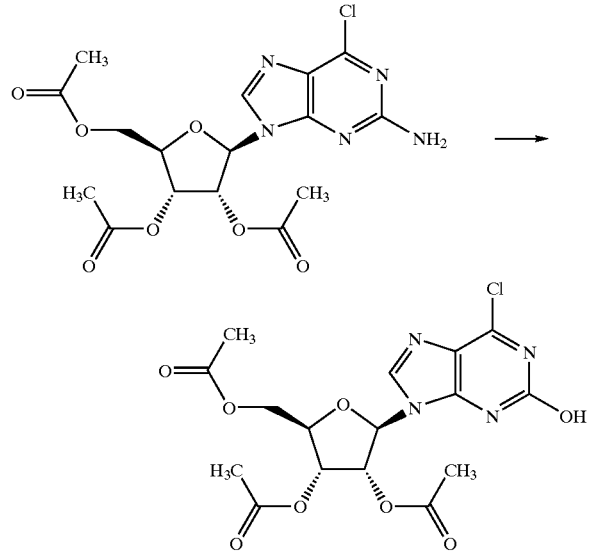

A suspension of 2-amino-6-chloro-9-(2,3,5-tri-O-acetyl-β-D-ribofuranosyl)purine (291.2 g, 0.68 mol, Example 1, Step B) in 2-propanol and water (1:1, 15,560 mL) which was heated to achieve homogeneity. The solution was cooled to <15° C. and then t-butyl nitrite (357 mL, 3.0 mol) was added. The reaction was allowed to warm to room temperature and stirred until the evolution of gas subsided. The reaction was partitioned between ethyl acetate (7,300 mL) and water and the phases allowed to separate. The aqueous layer was further extracted with ethyl acetate (2×7,300 mL) and the combined organic layers were dried over magnesium sulfate, filtered and removed under reduced pressure to yield a viscous oil. Typical Yield: Quantitative.

Step D: Preparation of 6-chloro-2-[2-(4-chlorophenyl) ethoxy]-9-(2,3,5-tri-O-acetyl-β-D-ribofuranosyl)purine

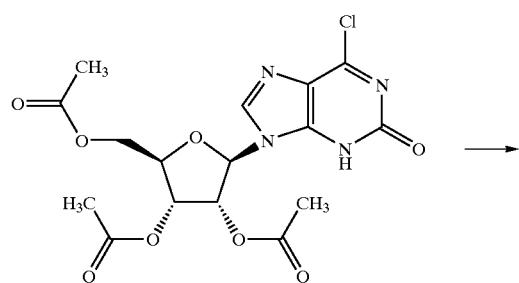

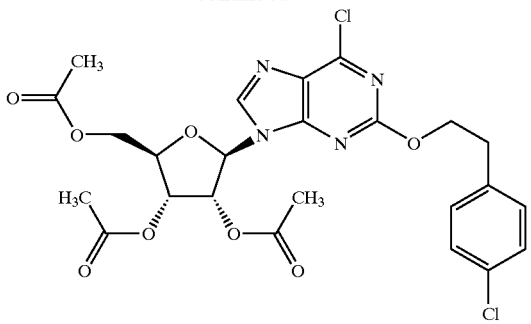

To a mixture of 6-chloro-2-hydroxy-9-(2,3,5-tri-O-acetyl-β-D-ribofuranosyl)purine (Example 2, Step C) and 2-(4-chlorophenyl)ethyl bromide (300.1 g, 1.36 mol) in dimethylformamide (7,280 mL), cesium carbonate (665 g, 2.04 mol) was added. The reaction was allowed to stir under inert atmosphere for 32 hours. The reaction was concentrated under reduced pressure and partitioned between dichloromethane and water. The organic layer was dried over magnesium sulfate, filtered, and evaporated under reduced pressure. The crude product was purified by column chromatography eluting with ethyl acetate/heptanes to yield a yellow solid of 6-chloro-2-[2-(4-chlorophenyl)ethoxy]-9-(2,3,5-tri-O-acetyl-β-D-ribofuranosyl)purine Typical Yield: 64%

Step E: Preparation of 2-[2-(4-chlorophenyl)ethoxy] adenosine

A reactor was charged with 6-chloro-2-[2-(4-chlorophenyl)ethoxy]-9-(2,3,5-tri-O-acetyl-β-D-ribofuranosyl)purine (243.8 g, 0.43 mol, Example 2, Step D) in ethanol (3,660 mL). The reactor was chilled to below −33° C., and ammonia (1500 g) is charged into the reactor. The reactor was sealed, then heated to 100° C. and the reaction was monitored by HPLC. Upon completion (approximately 5 hours), the reactor was cooled, vented, and the contents concentrated under reduced pressure. The crude product is purified by column chromatography eluting with dichloromethane/methanol. The pure fractions were concentrated under reduced pressure to about four liters of solvent and the product collected by vacuum filtration. The off-white solid was washed with dichloromethane and dried in vacuo to yield 82 grams of analytically pure (>99%) product as an off-white solid. Additional fractions were combined to provide an additional 73 g of product of lower purity (90–98%). Combined typical yield: 54%.

EXAMPLES 3–16

Additional Syntheses

By utilizing procedures of Examples 1 and 2 above, additional compounds were synthesized as specified in the following Examples 3–18. The chemical structure of each of the synthesized compounds is specified below with the general formula of the compounds shown at the top of the examples (a first structure shown for Examples 3–8, a second structure shown for Examples 9–16).

EXAMPLES 3–8

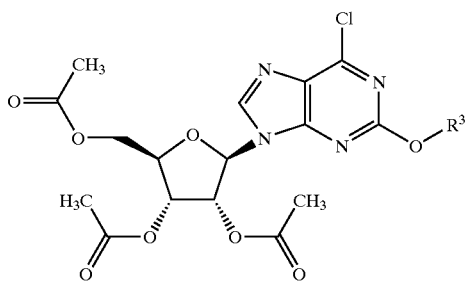

EXAMPLE 3

Preparation of 2-benzyloxy-6-chloro-9-(2,3,5-tri-O-acetyl-β-D-ribofuranosyl)purine

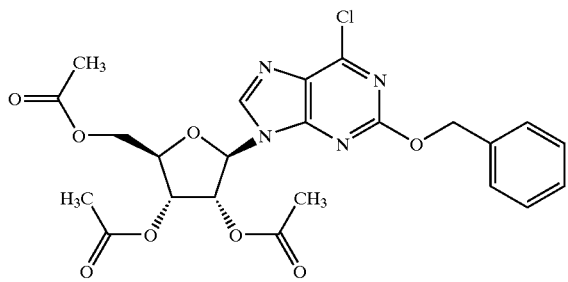

A compound having a structure of the above formula was prepared where the substituent $R^3$ is —$CH_2C_6H_5$ (benzyl) by using as an alkylating agent benzyl bromide. The compound ($C_{23}H_{23}ClN_4O_8$) was isolated as an oil in 65% yield from the deamination and alkylation of 2-amino-6-chloro-9-(2,3,5-tri-O-acetyl-β-D-ribofuranosyl)purine (Example 1, Step B) following the general procedure described in Example 2, Steps C and D. $^1$H-NMR (DMSO-$d_6$): δ 1.93 (s, 3H); 2.10 (s, 3H); 2.16 (s, 3H); 4.25 (m, 1H); 4:39 (m, 2H); 5.47 (s, 2H); 5.76 (t, 1H, J=6); 6.00 (t, 1H, J=6); 6.27 (d, 1H, J=6); 7.45 (m, 5H); 8.64 (s, 1H).

EXAMPLE 4

Preparation of 6-chloro-2-(4-nitrobenzyloxy)-9-(2,3,5-tri-O-acetyl-β-D-ribofuranosyl)purine

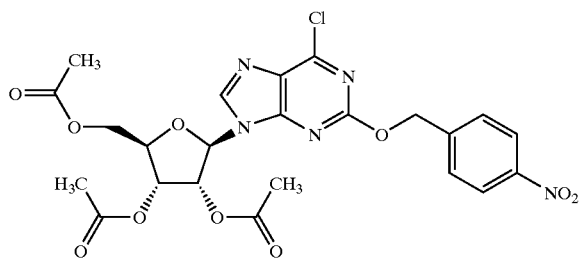

A compound having a structure of the above formula was prepared where the substituent $R^3$ is —$CH_2(4\text{-}NO_2C_6H_4)$ (4-nitrobenzyl) by using as an alkylating agent 4-nitrobenzyl bromide. The compound ($C_{23}H_{22}ClN_5O_{10}$) was isolated in 60% yield from the deamination and alkylation of 2-amino-6-chloro-9-(2,3,5-tri-O-acetyl-β-D-ribofuranosyl)purine (Example 1, Step B) following the general procedure described in Example 2, Steps C and D as a solid with melting point of 178–180° C. $^1$H-NMR (DMSO-$d_6$): δ 1.94 (s, 3H); 2.05 (s, 3H); 2.11 (s, 3H); 4.10 (m, 1H); 4.33 (m, 2H); 5.65 (s, 2H); 5.72 (t, 1H, J=6); 5.97 (t, 1H, J=6); 6.26 (d, 1H, J=4); 7.74 (d, 2H, J=8); 8.27 (d, 2H, J=8); 8.66 (s, 1H).

EXAMPLE 5

Preparation of 2-butyloxy-6-chloro-9-(2,3,5-tri-O-acetyl-β-D-ribofuranosyl)purine

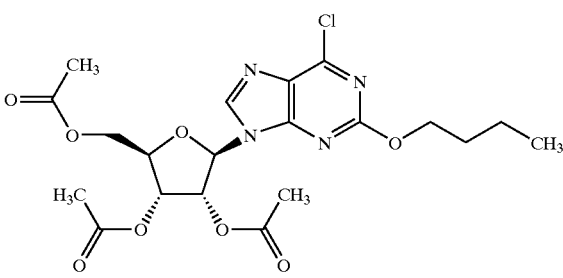

A compound having a structure of the above formula was prepared where the substituent $R^3$ is —$CH_2CH_2CH_2CH_3$ (n-butyl) by using as an alkylating agent 1-bromobutane. The compound ($C_{20}H_{25}ClN_4O_8$) was isolated as an oil in 55% yield from the deamination and alkylation of 2-amino-6-chloro-9-(2,3,5-tri-O-acetyl-β-D-ribofuranosyl)purine (Example 1, Step B) following the general procedure described in Example 2, Steps C and D. $^1$H-NMR (DMSO-$d_6$): δ 0.89 (t, 3H, J=6); 1.42 (m, 2H); 1.73 (m, 2H); 1.95 (s, 3H); 2.06 (s, 3H); 2.10 (s, 3H); 4.00 (m, 1H); 4.20 (m, 2H); 4.40 (m, 2H); 5.72 (t, 1H, J=6); 5.99 (t, 1H, J=6); 6.25 (d, 1H, J=4); 8.61 (s, 1H).

EXAMPLE 6

Preparation of (6-chloro-9-(2,3,5-tri-O-acetyl-β-D-ribofuranosyl)purin-2-yl)oxyacetic acid tert-butyl ester

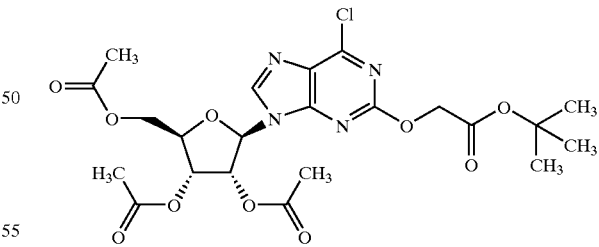

A compound having a structure of the above formula was prepared where the substituent $R^3$ is —$CH_2C(\!=\!O)OC(CH_3)_3$ by using as an alkylating agent tert-butyl bromoacetate (—$BrCH_2C(\!=\!O)OC(CH_3)_3$). The compound ($C_{22}H_{27}ClN_4O_{10}$) was isolated as an oil in 40% yield from the deamination and alkylation of 2-amino-6-chloro-9-(2,3,5-tri-O-acetyl-β-D-ribofuranosyl)purine (Example 1, Step B) following the general procedure described in Example 2, Steps C and D.

EXAMPLE 7

Preparation of 6-chloro-2-[3-(3-methoxyphenyl)propyloxy]-9-)2,3,5-tri-O-acetyl-β-D-ribofuranosyl

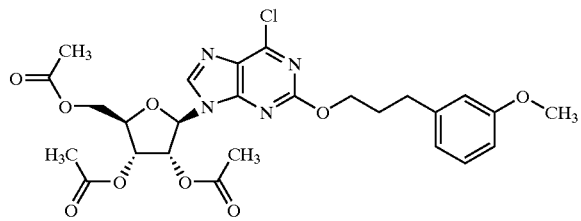

A compound having a structure of the above formula was prepared where the substituent $R^3$ is $CH_2CH_2CH_2(3\text{-}OCH_3)C_6H_4$ by using as an alkylating agent 3-(3-methoxyphenyl)propyl bromide (—$BrCH_2CH_2CH_2(3\text{-}OCH_3)C_6H_4$). The compound ($C_{26}H_{29}ClN_4O_9$) was isolated in 30% yield as an oil from the deamination and alkylation of 2-amino-6-chloro-9-(2,3,5-tri-O-acetyl-β-D-ribofuranosyl)purine (Example 1, Step B) following the general procedure described in Example 2, Steps C and D.

EXAMPLE 8

Preparation of 2-[4-(tert-butyl)benzyloxy]-6-chloro-9-(2,3,5-tri-O-acetyl-β-D-ribofuranosyl)purine

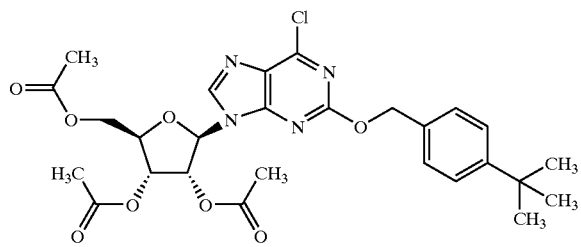

A compound having a structure of the above formula was prepared where the substituent $R^3$ is —$CH_2\text{-}4\text{-}(C(CH_3)_3)C_6H_4$ (4-tert-butylbenzoyl) by using as an alkylating agent 4-(tert-butyl)benzyl bromide (—$BrCH_2\text{-}4\text{-}(C(CH_3)_3)C_6H_4$). The compound ($C_{27}H_{31}ClN_4O_8$) was isolated as a solid with melting point 58–60° C. in 45% yield from the deamination and alkylation of 2-amino-6-chloro-9-(2,3,5-tri-O-acetyl-β-D-ribofuranosyl)purine (Example 1, Step B) following the general procedure described in Example 2, Steps C and D. $^1$H-NMR (DMSO-$d_6$): δ 1.32 (s, 9H); 2.08 (s, 3H); 2.10 (s, 3H); 2.15 (s, 3H); 4.37 (m, 3H); 5.48 (s, 2H); 5.63 (t, 1H, J=6); 5.89 (t, 1H, J=6); 6.15 (d, 1H, J=4); 7.43 (bs, 4H); 8.09 (s, 1H).

EXAMPLES 9–16

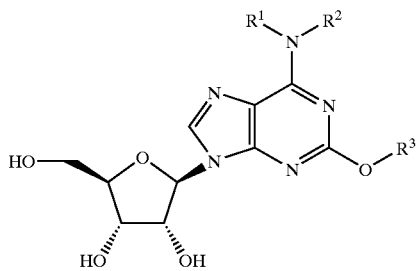

EXAMPLE 9

Preparation of 2-benzyloxyadenosine

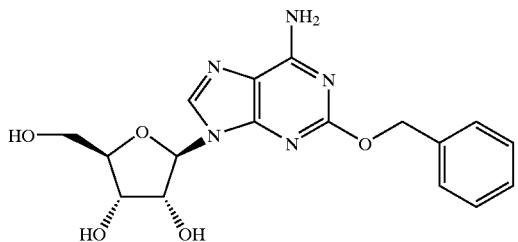

A compound having a structure of the above formula was prepared where the substituents $R^1$ and $R^2$ are hydrogen and $R^3$ is benzyl (—$CH_2C_6H_5$). The compound ($C_{17}H_{19}N_5O_5$) was prepared by reaction of ammonia with 2-benzyloxy-6-chloro-9-(2,3,5-tri-O-acetyl-β-D-ribofuranosyl)purine (Example 3) as described in Example 2, Step E. The final product was isolated in 70% yield as a solid with melting point of 178–179 ° C. $^1$H-NMR (DMSO-$d_6$): δ 3.49 (m, 1H); 3.61 (m, 1H); 3.9 (m, 1H); 4.12 (m, 1H); 4.58 (m, 1H); 5.18 (d, 2H, J=4); 5.3 (s, 2H); 5.42 (d, 1H, J=6); 5.79 (d, 1H, J=6); 7.37 (m, 7H); 8.16 (s, 1H).

EXAMPLE 10

Preparation of 2-benzyloxy-$N^6$-ethyladenosine

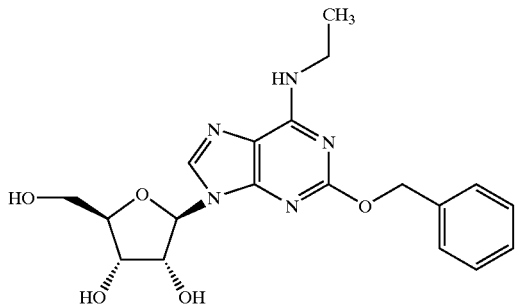

A compound having a structure of the above formula was prepared where the substituent $R^1$ is —$CH_2CH_3$, $R^2$ is hydrogen, and $R^3$ is benzyl (—$CH_2C_6H_5$). The compound ($C_{19}H_{23}N_5O_5$) was prepared by reaction of ethylamine with 2-benzyloxy-6-chloro-9-(2,3,5-tri-O-acetyl-β-D-ribofuranosyl)purine (Example 3) as described in Example 2, Step E. The final product was isolated in 40% yield as a solid with melting point of 170–171° C. $^1$H-NMR (DMSO-$d_6$): δ 1.13 (t, 3H, J=8); 3.6 (m, 4H); 3.9 (m, 1H); 4.1 (m, 1H); 4.5 (m, 1H); 5.18 (m, 2H); 5.32 (s, 2H); 5.42 (d, 1H, J×6); 5.78 (d, 1H, J=6); 7.41 (m, 5H); 7.93 (bm, 1H); 8.15 (s, 1H).

EXAMPLE 11

Preparation of 2-(4-nitrobenzyl)oxy-$N^6$-ethyladenosine

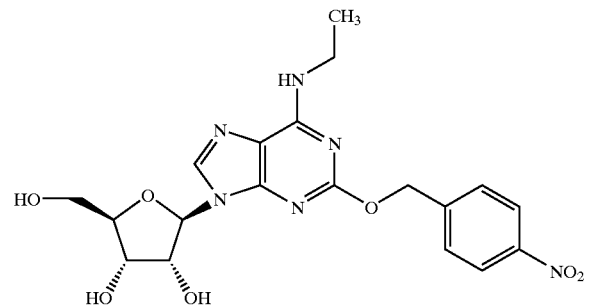

A compound having a structure of the above formula was prepared where the substituent $R^1$ is —$CH_2CH_3$, $R^2$ is hydrogen, and $R^3$ is 4-nitrobenzyl (—$CH_2$(4-nitro)$C_6H_4$). The compound ($C_{19}H_{22}N_6O_7$) was prepared by reaction of ethylamine with 6-chloro-2-(4-nitrobenzyl)oxy-9-(2,3,5-tri-O-acetyl-β-D-ribofuranosyl)purine (Example 4) as described in Example 2, Step E. The final product was isolated in 60% yield as a solid with a melting point of 210–213° C. $^1$H-NMR (DMSO-$d_6$): δ 1.05 (1, 3H, J=8); 3.4 (m, 2H); 3.5 (m, 1H); 3.6 (m, 1H); 3.85 (m, 1H); 4.05 (m, 1H); 4.6 (m, 1H); 5.2 (m, 2H); 5.4 (d, 1H, J=6); 5.45 (s, 2H); 5.8 (d, 1H, J=6); 7.8 (d, 2H, J=8); 8 (bt, 1H); 8.2 (s, 1H); 8.25 (d, 2H, J=8).

EXAMPLE 12

Preparation of 2-(4-nitrobenzyl)oxyadenosine

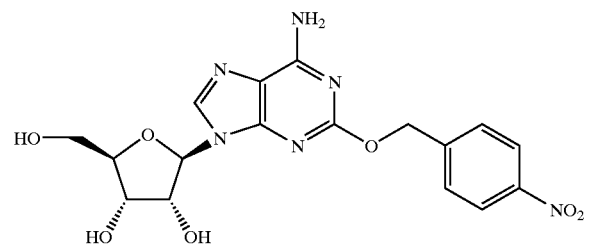

A compound having a structure of the above formula was prepared where the substituents $R^1$ and $R^2$ are hydrogen and $R^3$ is 4-nitrobenzyl (—$CH_2$(4-nitro)$C_6H_4$). The compound ($C_{17}H_{18}N_6O_7$) was prepared by reaction of ammonia with 6-chloro-2-(4-nitrobenzyl)oxy-9-(2,3,5-tri-O-acetyl-β-D-ribofuranosyl)purine (Example 4) as described in Example 2, Step E. The final product was isolated in 80% yield as a solid with a melting point of 174–176° C. $^1$H-NMR (DMSO-$d_6$): δ 3.5 (m, 1H); 3.6 (m, 1H); 3.8 (d, 1H, J=4); 4.1 (m, 1H); 4.56 (m, 1H); 5.16 (m, 2H); 5.4 (d, 1H, J=6); 5.47 (s, 2H); 5.77 (d, 1H, J=6); 7.43 (bs, 2H); 7.7 (d, 2H, J=8); 8.18 (s, 1H); 8.24 (d, 2H, J=8).

EXAMPLE 13

Preparation of 2-butyloxyadenosine

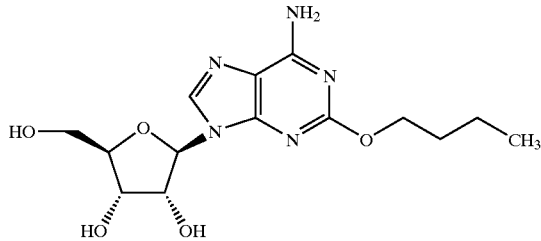

A compound having a structure of the above formula was prepared where the substituents $R^1$ and $R^2$ are hydrogen and $R^3$ is n-butyl (—$CH_2CH_2CH_2CH_3$). The compound ($C_{14}H_{21}N_5O_5$) was prepared by reaction of ammonia with 2-butyloxy-6-chloro-9-(2,3,5-tri-O-acetyl-β-D-ribofuranosyl)purine (Example 5) as described in Example 2, Step E. The final product was isolated in 30% yield as a solid with a melting point of 145–146° C. $^1$H-NMR (DMSO-$d_6$): δ 0.9 (t, 3H); 1.37 (m, 2H, J=8); 1.65 (m, 2H, J=8); 3.66 (m, 2H); 3.97 (m, 1H); 4.18 (m, 3H); 4.57 (m, 1H), 4.95 (d, 1H, J=6); 5.23 (m, 2H); 5.78 (d, 1H, J=6); 6.9 (bs, 2H); 7.94 (s, 1H).

EXAMPLE 14

Preparation of 2-carboxymethoxyadenosine

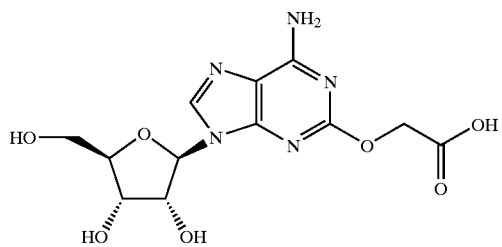

A compound having a structure of the above formula was prepared where the substituents $R^1$ and $R^2$ are hydrogen and $R^3$ is —$CH_2COOH$. The compound ($C_{12}H_{15}N_5O_7$) was prepared by reaction of ammonia with (6-chloro-9-(2,3,5-tri-O-acetyl-β-D-ribofuran-osyl)purin-2-yl)oxyacetic acid tert-butyl ester (Example 6) as described in Example 2, Step E. The final product was isolated in 70% yield as a solid with a melting point of 200–203° C. $^1$H-NMR (DMSO-$d_6$): δ 3.4 (m, 1H); 3.55 (m, 1H); 3.91 (m, 1H); 4.11 (m, 1H); 4.56 (m, 1H); 4.74 (bs, 1H); 4.78 (s, 2H); 5.3 (bs, 2H); 5.75 (d, 1H, J=6); 7.36 (bs, 2H); 8.15 (s, 1H); 12.6 (bs, 1H).

EXAMPLE 15

Preparation of 2-[3-(3-methoxyphenyl)propyloxy]adenosine

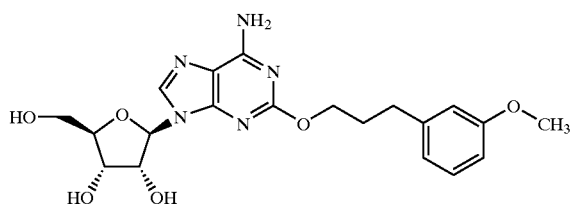

A compound having a structure of the above formula was prepared where the substituents $R^1$ and $R^2$ are hydrogen and $R^3$ is —$CH_2CH_2CH_2(3\text{-}OCH_3)C_6H_4$. The compound ($C_{20}H_{25}N_5O_6$) was prepared by reaction of ammonia with 6-chloro-2-[3-(3-methoxyphenyl)propyloxy]-9-(2,3,5-tri-O-acetyl-β-D-ribofuranosyl)purine (Example 7) as described in Example 2, Step E. The final product was isolated in 10% yield as a solid with a melting point of 85–87° C. $^1$H-NMR (DMSO-$d_6$): 1.97 (t, 2H, J=6); 2.69 (t, 2H, J=6); 3.54 (m, 2H); 3.71 (s, 3H); 3.95 (m, 1H); 4.15 (m, 3H); 4.58 (m, 1H); 5.19 (m, 2H); 5.42 (d, 1H, J=6); 5.77 (d, 1H, J=6); 6.77 (m, 3H); 7.19 (t, 1H, 8); 7.3 (bs, 2H); 8.14 (s, 1H).

EXAMPLE 16

Preparation of 2-[4-(tert-butyl)benzyloxy]-$N^6$-cyclopentyladenosine

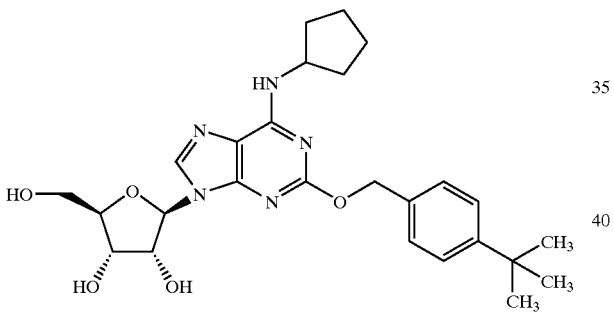

A compound having a structure of the above formula was prepared where the substituent $R^1$ is cyclopentyl, $R^2$ is hydrogen, and $R^3$ is —$CH_2(4\text{-}(C(CH_3)_3)C_6H_4$ (4-tert-butylbenzoyl). The compound ($C_{25}H_{35}N_5O_5$) was prepared by reaction of cyclopentylamine with 2-[4-(tert-butyl)benzyloxy]-6-chloro-9-(2,3,5-tri-O-acetyl-β-D-ribofuranosyl)purine (Example 8) as described in Example 2, Step E. The final product was isolated in 50% yield as a solid with a melting point of 118–120° C. $^1$H-NMR (CDCl$_3$): 1.3 (s, 9H); 1.6 (m, 6H); 2.0 (m, 2H); 3.46 (m, 3H); 3.75 (m, 1H); 3.89 (m, 1H); 4.28 (s, 1H); 4.42 (m, 2H); 5.1 (m, 1H); 5.29 (s, 2H); 5.7 (d, 1H); 5.7 (m, 1H); 7.35 (s, 4H); 7.57 (bs, 1H).

The following citations have been referred to herein. These references are incorporated herein by reference in their entirety.

1. Montesinos, M. C.; Gadangi, P.; Longaker, M.; Sung, J.; Levine, J.; Nilsen, D.; Reibman, J.; Li, M.; Jiang, C.-K.; Hirschhorn, R.; Recht, P. A.; Ostad, E.; Levin, R. I.; Cronstein, B. N. Wound healing is accelerated by agonists of adenosine $A_2$ ($G_{αs}$-linked) receptors. *J. Exp. Med.*, 1997, 186, 1615–1620.
2. Marumoto, R.; Yoshioka, Y.; Miyashita, O.; Shima, S.; Imai, K.; Kawazoe, K.; Honjo, M., Synthesis and coronary vasodilating activity of 2-substituted adenosines. *Chem. Pharm. Bull.* 1975 23, 759–774.
3. Ueeda, M.; Thompson, R. D.; Arroyo, L. H.; Olsson, R. A. 2-Alkoxyadenosines: Potent and selective agonists at the coronary artery $A_2$ adenosine receptor. *J. Med. Chem.*, 1991, 34, 1334–1339.
4. Ueeda, M.; Thompson, R. D.; Arroyo, L. H.; Olsson, R. A., 2-Aralkyloxyadenosines: Potent and selective agonists at the coronary artery $A_2$ adenosine receptor. *J. Med. Chem.*, 1991, 34, 1340–1344.

The invention has been described in detail with reference to preferred embodiments thereof. However, it will be appreciated that those skilled in the art, upon consideration of the disclosure, may make modifications and improvements within the spirit and scope of the invention.

What is claimed is:

1. A method for synthesis of a 2-aralkyloxyadenosine or a 2-alkoxyadenosine, comprising:

(a) activating a guanosine compound by halogenation of the aglycone to yield a halogenated compound;

(b) hydrolyzing the halogenated compound by diazotization of the 2-amino moiety of the halogenated compound to yield a 2-hydroxy compound;

(c) treating the 2-hydroxy compound with an alkylating agent to yield an alkylated compound; and (d) treating the alkylated compound with ammonia or an amine to provide a 2-aralkyloxyadenosine or a 2-alkoxyadenosine compound.

2. The method of claim 1 wherein the 2-aralkyloxyadenosine or a 2-alkoxyadenosine compound has a structure of the following Formula I:

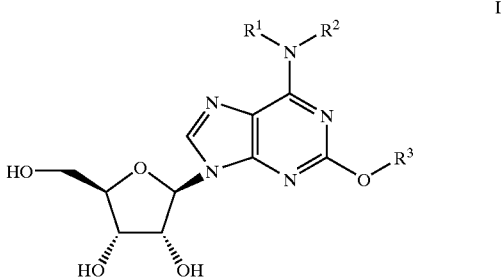

wherein:

$R^1$ and $R^2$ are independently hydrogen, alkyl, substituted alkyl, alkenyl, substituted alkenyl, alkynyl, substituted akynyl, cycloalkcyl, substituted cycloalkyl, cycloalkenyl, substituted cycloalkenyl, aralkyl, substituted aralkyl, aryl, substituted aryl, heteroaryl, heterocyclic, or if taken together with the nitrogen atom, forms an azetidine ring or a 5–6 membered heterocyclic ring containing a total of one to four heteroatoms selected from nitrogen, oxygen, and sulfur; $R^3$ is alkyl, substituted alkyl, alkenyl, substituted alkenyl, alkynyl, substituted alkynyl, aralkyl, substituted aralkyl, aralkenyl, or substituted aralkenyl.

3. The method of claim 1 wherein the product of step (d) is 2-[2-(4-chlorophenyl)ethoxy]adenosine.

4. A process for the preparation of a compound of formula I:

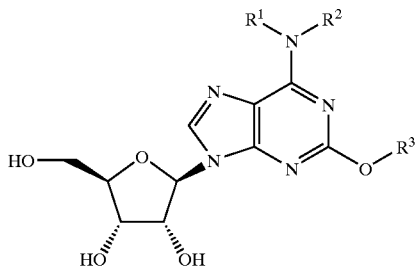

wherein:

$R^1$ and $R^2$ are independently hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aralkyl, substituted aralkyl, aryl, substituted aryl, heteroaryl, heterocyclic, or if taken together with the nitrogen atom, forms an azetidine ring or a 5–6 membered heterocyclic ring containing a total of one to four heteroatoms selected from nitrogen, oxygen, and sulfur;

$R^3$ is alkyl, substituted alkyl, alkenyl, substituted alkenyl, alkynyl, substituted alkynyl, aralkyl, substituted aralkyl, aralkenyl, or substituted aralkenyl; the method comprising:

(a) treating guanosine with an acylating agent to yield an alkylated compound;

(b) treating the alkylated compound with a halide source to yield a halogenated compound;

(c) hydrolyzing the halogenated compound to yield a hydrolyzed compound;

(d) treating the hydrolyzed compound with an alkylating agent to yield an alkylated compound; and (e) treating the alkylated compound with ammonia or an amine to provide the compound of Formula I.

5. The process of claim 4 wherein the product of step (e) is 2-[2-(4-chlorophenyl)ethoxy]adenosine.

6. The process of claim 4 or 5 wherein in step (e), the alkylated compound is treated with ammonia.

7. The process of claim 4 or 5 wherein the acylating agent is an acid halide or an acid anhydride.

8. The process of claim 4 or 5 wherein the acylation is conducted under basic conditions.

9. The process of claim 4 or 5 wherein the halide source is a chloride source.

10. The process of claim 9 wherein the chloride source is selected from the group consisting of phosphorus oxychloride, thionyl chloride, phosphorus pentachloride, chlorine gas, carbon tetrachloride/triphenylphosphine, dichlorotriphenylphosphorane, or triphenylantimony dichloride.

11. The process of claim 4 or 5 wherein the hydrolysis follows diazotization.

12. The process of claim 11 wherein the diazotization is conducted in the presence of a nitrite reagent.

13. A process for the preparation of a compound of formula I:

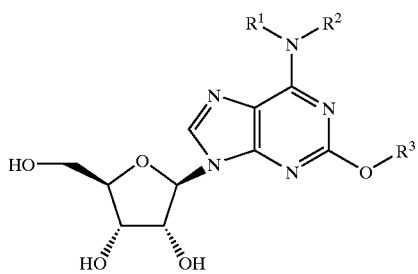

wherein:

$R^1$ and $R^2$ are independently hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aralkyl, substituted aralkyl, aryl, substituted aryl, heteroaryl, heterocyclic, or if taken together with the nitrogen atom, forms an azetidine ring or a 5–6 membered heterocyclic ring containing a total of one to four heteroatoms selected from nitrogen, oxygen, and sulfur;

$R^3$ is alkyl, substituted alkyl, alkenyl, substituted alkenyl, alkynyl, substituted alkynyl, aralkyl, substituted aralkyl, aralkenyl, or substituted aralkenyl; comprising the steps of:

(a) treating guanosine with an acylating agent in the presence of a base and a solvent at a reaction temperature of about 20° C. to about 120° C. for a period of about 20 minutes to about 30 hours;

(b) treating the product of step (a) in a solvent with a suitable chloride source, such as phosphorus oxychloride in the presence of a tertiary amine, thionyl chloride/DMF, phosphorus pentachloride, chlorine gas, carbon tetrachloride/triphenylphosphine, dichlorotriphenylphosphorane, or triphenylantimony dichloride at a reaction temperature of 10° C. to about 120° C. for a period of about 5 minutes to about 8 hours;

(c) hydrolytic diazotization of the product from step (b) with an alkyl nitrite or sodium nitrite and an inorganic acid in a mixture of water and a lower alcohol at −10° C. to about 60° C. for a period of about 20 minutes to about 24 hours;

(d) adding to the protected 6-chloro-2-hydroxy-9-(β-D-ribofuranosyl)-purine in a solvent, a base and a suitable alkylating agent, at a temperature of 10° C. to about 120° C. for a period of about 30 minutes to about 48 hours;

(e) dissolving the intermediate of step (d) in an alcoholic solvent which is then treated with ammonia or a suitable primary or secondary amine at temperatures of −70° C. to about 120° C. for a period of about 20 minutes to about 48 hours and one to fifty atmospheres of pressure; evaporating the reaction mixture; then purifying the product by recrystallization from an appropriate solvent or chromatography or a combination of these two methods.

14. The process of claim 13 wherein the acylating agent in step (a) is selected from the group consisting of acetyl chloride, acetic anhydride, propionyl chloride, propionic anhydride, benzoyl chloride, benzoic anhydride, phenylacetyl chloride, and phenoxyacetyl chloride.

15. The process of claim 13 wherein the base in step (a) is selected from the group consisting of pyridine, 4-dimethylaminopyridine, 4-pyrrolidinyl-pyridine, N,N-dimethylaniline, N-ethyl-N-methylaniline, N,N-diethylaniline, trimethylamine, triethylamine, N,N-dimethylethyl amine, N,N-dimethyl-isopropyl amine, and N,N-diethylmethyl amine.

16. The process of claim 13 wherein the solvent in step (a) is selected from the group consisting of dimethylformamide, dimethylacetamide, pyridine, acetonitrile, tetrahydrofuran, hexamethylphosphoramide, and 1,4-dioxane.

17. The process of claim 13 wherein the solvent in step (b) is selected from the group consisting of acetonitrile, dichloromethane, chloroform, carbon tetrachloride, 1,2-dimethoxyethane, tetrahydrofuran, dimethylformamide, hexamethylphosphoramide, 1,4-dioxane, 1,2-dichloroethane, di(ethylene glycol) diethyl ether, and 2-methoxyethyl ether.

18. The process of claim 13 wherein in step (b) the chloride source is selected from the group consisting of phosphorus oxychloride, thionyl chloride, phosphorus pentachloride, chlorine gas, carbon tetrachloride/triphenylphosphine, dichlorotriphenylphosphorane, or triphenylantimony dichloride.

19. The process of claim 13 wherein in step (b) the tertiary amine is selected from the group consisting of N,N-dimethylaniline, N-ethyl-N-methylaniline, N,N-diethylaniline, trimethylamine, triethylamine, N,N-dimethylethyl amine, N,N-dimethylisopropyl amine, and N,N-diethylmethyl amine.

20. The process of claim 13 wherein in step (c) the alkyl nitrite is selected from the group consisting of tert-butyl nitrite, amyl nitrite, iso-amyl nitrite, and n-butyl nitrite.

21. The process of claim 13 wherein in step (c) the lower alcohol is selected from the group consisting of methanol, ethanol, 1-propanol, 2-propanol, 1-butanol, 2-butanol, tert-butanol, amyl alcohol, and isoamyl alcohol.

22. The process of claim 13 wherein in step (c) the inorganic acid is selected from the group consisting of hydrochloric acid, hydrobromic acid, nitric acid, and sulfuric acid.

23. The process of claim 13 wherein in step (d) the base is selected from the group consisting of lithium carbonate, sodium carbonate, potassium carbonate, cesium carbonate, sodium hydroxide, potassium hydroxide, sodium hydride, sodium tert-butoxide, and potassium tert-butoxide.

24. The process of claim 13 wherein in step (d) the solvent is selected from the group consisting of dimethylformamide, dimethylacetamide, dimethylsulfoxide, hexamethylphosphoramide, 1,2-dimethoxyethane, 1,4-dioxane, tetrahydrofuran, and 2-methoxyethyl ether.

25. The process of claim 13 wherein in step (e) the alcoholic solvent is selected from the group consisting of methanol, ethanol, 1-propanol, and 2-propanol.

26. A process for the preparation of 2-[2-(4-chlorophenyl) ethoxy]adenosine comprising:
  (a) treating guanosine with an acylating agent in the presence of a base and a solvent at a reaction temperature of about 20° C. to about 120° C. for a period of about 20 minutes to about 30 hours;
  (b) treating the product of step (a) in a solvent with a suitable chloride source at a reaction temperature of 10° C. to about 120° C. for a period of about 5 minutes to about 8 hours;
  (c) hydrolytic diazotization of the product from step (b) with an alkyl nitrite or sodium nitrite and an inorganic acid in a mixture of water and a lower alcohol at −10° C. to about 60° C. for a period of about 20 minutes to about 24 hours;
  (d) adding to the protected 6-chloro-2-hydroxy-9-(β-D-ribofuranosyl)purine in a solvent, a base and a suitable alkylating agent, at a temperature of 0° C. to about 120° C. for a period of about 30 minutes to about 48 hours;
  (e) dissolving the intermediate of step (d) in an alcoholic solvent which is then treated with ammonia or a suitable primary or secondary amine at temperatures of −70 ° C. to about 120° C. for a period of about 20 minutes to about 48 hours and one to fifty atmospheres of pressure; evaporating the reaction mixture; then purifying the product by recrystallization from an appropriate solvent or chromatography or a combination of these two methods.

27. The process of claim 26 wherein in step (a) the acylating agent is selected from the group consisting of acetyl chloride, acetic anhydride, propionyl chloride, propionic anhydride, benzoyl chloride, benzoic anhydride, phenylacetyl chloride, and phenoxyacetyl chloride.

28. The process of claim 26 wherein in step (a) the base is selected from the group consisting of pyridine, 4-dimethylaminopyridine, 4-pyrrolidinyl-pyridine, N,N-dimethylaniline, N-ethyl-N-methylaniline, N,N-diethylaniline, trimethylamine, triethylamine, N,N-dimethylethyl amine, N,N-dimethyl-isopropyl amine, and N,N-diethylmethyl amine.

29. The process of claim 26 wherein in step (a) the solvent is selected from the group consisting of dimethylformamide, dimethylacetamide, pyridine, acetonitrile, tetrahydrofuran, hexamethylphosphoramide, and 1,4-dioxane.

30. The process of claim 26 wherein in step (b) the solvent is selected from the group consisting of acetonitrile, dichloromethane, chloroform, carbon tetrachloride, 1,2-dimethoxyethane, tetrahydrofuran, dimethylformamide, hexamethylphosphoramide, 1,4-dioxane, 1,2-dichloroethane, di(ethylene glycol) diethyl ether, and 2-methoxyethyl ether.

31. The process of claim 26 wherein the step (b) the chloride source is selected from the group consisting of phosphorus oxychloride, thionyl chloride, phosphorus pentachloride, chlorine gas, carbon tetrachloride/triphenylphosphine, dichlorotriphenylphosphorane, or triphenylantimony dichloride.

32. The process of claim 26 wherein in step (b) the tertiary amine is selected from the group consisting of N,N-dimethylaniline, N-ethyl-N-methylaniline, N,N-diethylaniline, trimethylamine, triethylamine, N,N-diethylmethyl amine, N,N-dimethylisopropyl amine, and N,N-diethylmethyl amine.

33. The process of claim 26 wherein in step (c) the alkyl nitrite is selected from the group consisting of tert-butyl nitrite, amyl nitrite, iso-amyl nitrite, and n-butyl nitrite.

34. The process of claim 26 wherein in step (c) the lower alcohol is selected from the group consisting of methanol, ethanol, 1-propanol, 2-propanol, 1-butanol, 2-butanol, tert-butanol, amyl alcohol, and isoamyl alcohol.

35. The process of claim 26 wherein in step (c) the inorganic acid is selected from the group consisting of hydrochloric acid, hydrobromic acid, nitric acid, and sulfuric acid.

36. The process of claim 26 wherein in step (d) the base is selected from the group consisting of lithium carbonate, sodium carbonate, potassium carbonate, cesium carbonate, sodium hydroxide, potassium hydroxide, sodium hydride, sodium tert-butoxide, and potassium tert-butoxide.

37. The process of claim 26 wherein in step (d) the solvent is selected from the group consisting of dimethylformamide, dimethylacetamide, dimethylsulfoxide, hexamethylphosphoramide, 1,2-dimethoxyethane, 1,4-dioxane, tetrahydrofuran, and 2-methoxyethyl ether.

38. The process of claim 26 wherein in step (e) the alcoholic solvent is selected from the group consisting of methanol, ethanol, 1-propanol, and 2-propanol.

39. The process of claim 26 wherein in step (a) the acylating agent is acetic anhydride.

40. The process of claim 26 wherein in step (a) the base is pyridine.

41. The process of claim 26 wherein in step (a) the solvent is dimethylformamide.

42. The process of claim 26 wherein in step (a) the reaction temperature is about 90° C. to 100° C.

43. The process of claim 26 wherein in step (a) the reaction time is about 3 to 6 hours.

44. The process of claim 26 wherein in step (b) the solvent is acetonitrile.

45. The process of claim 26 wherein in step (b) the chloride source is phosphorus oxychloride.

46. The process of claim 26 wherein in step (b) the tertiary amine is N,N-dimethylaniline.

47. The process of claim 26 wherein in step (b) the reaction temperature is between 40° C. and 80° C.

48. The process of claim 26 wherein in step (b) the reaction time is between 5 minutes and 30 minutes.

49. The process of claim 26 wherein in step (c) the alkyl nitrite is tert-butyl nitrite.

50. The process of claim 26 wherein in step (c) the lower alcohol is tert-butyl alcohol.

51. The process of claim 26 wherein in step (c) the temperature is from 10° C. to 30° C.

52. The process of claim 26 wherein in step (c) the time is from 1 hour to 4 hours.

53. The process of claim 26 wherein in step (d) the solvent is dimethylformamide.

54. The process of claim 26 wherein the base is cesium carbonate.

55. The process of claim 26 wherein in step (d) the time is from 20 to 30 hours.

56. The process of claim 26 wherein in step (d) the temperature is from 15° C. to 30° C.

57. The process of claim 26 wherein in step (d) the alkylating agent is selected from the group consisting of 2-(4-chlorophenyl)ethyl chloride, 2-(4-chlorophenyl)ethyl bromide, 2-(4-chlorophenyl)ethyl iodide, 2-(4-chlorophenyl)ethyl mesylate, 2-(4-chlorophenyl)ethyl triflate, and 2-(4-chlorophenyl)ethyl tosylate.

58. The process of claim 26 wherein in step (e) the solvent is ethanol.

59. The process of claim 26 wherein in step (e) the amine is ammonia.

60. The process of claim 26 wherein in step (e) the temperature is between 60° C. and 110° C.

61. The process of claim 26 wherein in step (e) the pressure is between thirty and forty-five atmospheres of pressure.

62. The process of claim 6, wherein the acylating agent is an acid halide or an acid anhydride.

63. The process of claim 6, wherein the acylation is conducted under basic conditions.

64. The process of claim 7, wherein the acylation is conducted under basic conditions.

65. The process of claim 6, wherein the halide source is a chloride source.

66. The process of claim 7, wherein the halide source is a chloride source.

67. The process of claim 8, wherein the halide source is a chloride source.

68. The process of claim 67, wherein the chloride source is selected from the group consisting of phosphorus oxychloride, thionyl chloride, phosphorus pentachloride, chlorine gas, carbon tetrachloride/triphenylphosphine, dichlorotriphenylphosphorane, or triphenylantimony dichloride.

69. The process of claim 66, wherein the chloride source is selected from the group consisting of phosphorus oxychloride, thionyl chloride, phosphorus pentachloride, chlorine gas, carbon tetrachloride/triphenylphosphine, dichlorotriphenylphosphorane, or triphenylantimony dichloride.

70. The process of claim 67, wherein the chloride source is selected from the group consisting of phosphorus oxychloride, thionyl chloride, phosphorus pentachloride, chlorine gas, carbon tetrachloride/triphenylphosphine, dichlorotriphenylphosphorane, or triphenylantimony dichloride.

71. The process of claim 6 wherein the hydrolysis follows diazotization.

72. The process of claim 7, wherein the hydrolysis follows diazotization.

73. The process of claim 8 wherein the hydrolysis follows diazotization.

74. The process of claim 9 wherein the hydrolysis follows diazotization.

75. The process of claim 10 wherein the hydrolysis follows diazotization.

76. The process of claim 71 wherein the diazotization is conducted in the presence of a nitrite reagent.

77. The process of claim 72 wherein the diazotization is conducted in the presence of a nitrite reagent.

78. The process of claim 73 wherein the diazotization is conducted in the presence of a nitrite reagent.

79. The process of claim 74 wherein the diazotization is conducted in the presence of a nitrite reagent.

80. The process of claim 75 wherein the diazotization is conducted in the presence of a nitrite reagent.

* * * * *

UNITED STATES PATENT AND TRADEMARK OFFICE
CERTIFICATE OF CORRECTION

PATENT NO. : 6,951,932 B2
DATED : October 4, 2005
INVENTOR(S) : Allan R. Moorman It is certified that error appears in the above-identified patent and that said Letters Patent is hereby corrected as shown below:

<u>Title page,</u>
Item [57], ABSTRACT,
Line 7, "animation" should be -- amination --.

<u>Column 2,</u>
Line 38, "animation" should be -- amination --.

<u>Column 20,</u>
Line 57, "akynyl" should be -- alkynyl --, and "cycloalkcyl" should be -- cycloalkyl --.

<u>Column 21,</u>
Lines 36 and 37, "alkylated" should be -- acylated --.

Signed and Sealed this

Thirteenth Day of June, 2006

JON W. DUDAS
*Director of the United States Patent and Trademark Office*